United States Patent [19]

Marty et al.

[11] Patent Number: 4,520,225
[45] Date of Patent: May 28, 1985

[54] PROCESS FOR THE PRETREATMENT OF LIGHT OLEFIN FRACTIONS

[75] Inventors: Claude Marty; Philippe Engelhard, both of Le Havre, France

[73] Assignee: Compagnie Francaise de Raffinage, Paris, France

[21] Appl. No.: 551,187

[22] Filed: Nov. 14, 1983

[30] Foreign Application Priority Data

Nov. 12, 1982 [FR] France ................................ 82 19009

[51] Int. Cl.$^3$ ............................ C07C 3/18; C07C 7/00
[52] U.S. Cl. ..................................... 585/832; 585/312; 585/329; 585/519; 585/521; 585/525; 585/810
[58] Field of Search ............... 585/510, 511, 512, 517, 585/518, 519, 521, 522, 532, 525, 810, 832, 312, 585/324, 329, 313

[56] References Cited

U.S. PATENT DOCUMENTS

| | | | |
|---|---|---|---|
| 2,433,465 | 12/1947 | Leum et al. | 585/832 |
| 2,552,692 | 5/1951 | Schulze et al. | 585/832 |
| 3,257,473 | 6/1966 | Kovach | 585/832 |
| 3,367,987 | 2/1968 | Walsh | 585/832 |

Primary Examiner—Delbert E. Gantz
Assistant Examiner—A. Pal
Attorney, Agent, or Firm—Curtis, Morris & Safford

[57] ABSTRACT

The invention relates to a process for the pretreatment of a light olefin fraction, or of a mixture of such fractions, for the purpose of selectively removing the isobutene and butadiene present.

In accordance with the invention, the olefin fraction is contacted with boron trifluoride in the gas phase, under such conditions and for such a length of time that the isobutene and the butadiene will polymerize selectively, and the boron trifluoride and the isobutene and butadiene polymers obtained are then conventionally separated from the effluent.

20 Claims, 1 Drawing Figure

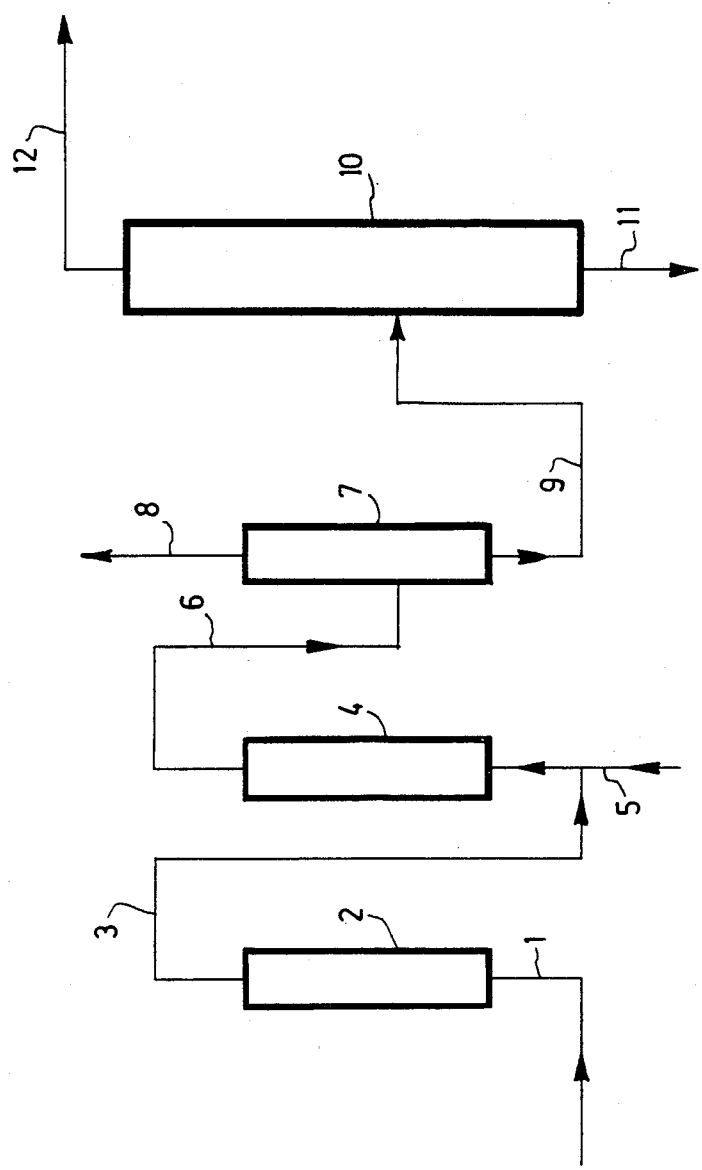

PROCESS FOR THE PRETREATMENT OF LIGHT OLEFIN FRACTIONS

The present invention relates to the pretreatment of petroleum charge stocks. More particularly, it has as its object a process for the pretreatment of light olefin fractions, or of mixtures of such fractions, for the purpose of selectively removing the isobutene and butadiene and thus upgrading these olefin fractions.

It is known that as a result of the recent development of cracking reactions for petroleum charge stocks large quantities of olefins having from two to eight carbon atoms, such as ethylene, propylene and the various butenes, pentenes, hexenes, heptenes and octenes, have become available. Of these, the olefin fractions with 3 and 4 carbon atoms, known as the $C_3-C_4$ and $C_4$ fractions, are in particularly great demand since they can be upgraded by a number of processes. For example, their oligomerization yields, after fractionation, starting materials of interest to the chemical industry, solvents, or lubricating oils; their alkylation results in products having a high octane number which go into the composition of premium-grade gasolines; and their dimerization also yields high-octane products, so far as the propylene fractions are concerned, and olefins having from 6 to 8 carbon atoms suitable for use as plasticizers, so far as the $C_3-C_4$ and the $C_4$ fractions are concerned.

However, in order that good use may be made of these olefin fractions, it is necessary that they first be purified since they are susceptible to the presence of many catalyst poisons, such as sulfur, nitrogen, isobutene or butadiene. Now while the sulfur derivatives (light mercaptans, $H_2S$, and COS) and the nitrogen derivatives (light amines) can be eliminated at least partially, it is very much more difficult to remove isobutene and butadiene, which produce gums and therefore are responsible for the rapid deactivation of catalysts. Moreover, the conversion of isobutene in oligomerization reactions, for example, leads to the formation of branched compounds, such as heptenes and octenes, which generally do not meet specifications.

The various pretreatments for light olefin charge stocks which have been proposed up to now in the literature (for example, in French patent application 2,421,157) usually are very costly and not very effective. They do not permit the complete removal of isobutene and the elimination of traces of butadiene.

Moreover, the pretreatment process in accordance with the present invention permits treating the olefin charge stocks at a much lower temperature, and more particularly at ambient temperature, which makes it possible to prevent parasitic isomerization of normal butenes to isobutene, and thus to avoid competing with the isobutene removal reaction which is the object of the present invention, to the detriment of the charge stock being treated.

The present invention thus provides a new, simple and economical process permitting the simultaneous and selective removal, under rather mild operating conditions, of isobutene and butadiene from light petroleum charge stocks containing them.

To this end, the invention has as its object a process for the pretreatment of a light olefin fraction, or of a mixture of such fractions, for the purpose of selective removal of the isobutene and butadiene which are present, said process being characterized in that the olefin fraction is contacted with boron trifluoride in the gas phase, under such conditions and for such a length of time that the isobutene and the butadiene will polymerize selectively; and in that the boron trifluoride and the polymers of isobutene and butadiene so obtained are then conventionally separated from the effluent.

Boron trifluoride catalysts supported on alumina are known as olefin polymerization catalysts from the literature. (See French Pat. No. 1,346,135.) They permit the polymerization reaction to be carried out under particularly mild conditions by comparison with other polymerization catalysts, such as phosphoric acid or hydrofluoric acid catalysts.

However, because of the presence of isobutene or butadiene in the charge stocks to be treated, which results in unwanted products or in off-grade reaction products, only limited use has been made of such alumina-supported boron trifluoride catalysts in oligomerization reactions involving light petroleum fractions.

In the process of the invention, which uses boron trifluoride in the gas phase, it is observed, however, that the boron trifluoride surprisingly acts on the isobutene and butadiene selectively to polymerize them, by a condensation reaction, without affecting the other olefins of $C_4$ and/or $C_3-C_4$ fractions.

Contacting the olefin charge stock with the boron trifluoride may be carried out in an enclosure in the presence of an inert filler material intended to increase the contact surfaces (for example, quartz pieces, glass beads, alumina beads, pebbles, etc.) and possibly to dissipate the heat evolved during the polymerization reaction.

The boron trifluoride can readily be separated from the effluent after the treatment, for example, by means of flash distillation. It is preferable to separate it first in order to prevent side reactions with the olefins.

The isobutene and butadiene polymers formed can then readily be separated conventionally, by fractionation, for purification of the $C_3-C_4$ or $C_4$ fractions. These charge stocks can then be subjected to oligomerization, alkylation, dimerization or other treatments without the usual operating difficulties outlined above being encountered, and with the service life of the catalysts used considerably extended.

The operating conditions of the process of the invention may be as follows, for example:

| | |
|---|---|
| Temperature: | 0 to 100° C. |
| Pressure: | 0 to 50 bars |
| Boron trifluoride concentration based on charge stock being treated: | 500 to 10,000 ppm |
| Hourly space velocity of charge stock: | 0.1 to 10 volumes per volume of filler material and per hour (v/v/h) |

It will be noted that these operating conditions are not very severe and, in pariticular, that the temperature may be equal or close to ambient temperature.

It is thus possible to selectively remove up to 95 percent of the isobutene and up to 100 percent of the butadiene present in the fractions being treated. The isobutene and butadiene polymers so separated from the $C_3-C_4$ or $C_4$ fractions are then readily upgraded. Fractionation, optionally followed by hydrogenation, then yields, based on boiling point: Dimers having a high octane number and usable in light gasolines; trimers suitable for use in the formulation of heavy gasolines and of solvents or in petrochemicals; tetramers which after hydrogenation will provide the bases for hydraulic fluids; and, finally, heavier polymers which, also after hydrogenation, are suitable for use as isoparaffinic oils.

Such selective polymerization of isobutene in relation to the n-butenes from mixtures of olefins contained in $C_3$–$C_4$ or $C_4$ fractions is not possible with the oligomerization catalysts commonly used in the industry, such as catalysts based on phosphoric esters. Since these catalysts are unstable at temperatures below 130° C., a pretreatment of these same olefin fractions with catalysts based on phosphoric esters and under operating conditions as close as possible to those used in accordance with the present application (reactor temperature, 130° C.; pressure, 40 bars; hourly space velocity of the charge stock, 3 v/v/h) would result in conversion rates of over 95 percent for isobutene and over 80 percent for the n-butenes.

As has been pointed out above, the pretreatment in accordance with the invention can be applied to any light olefin fraction which is intended to undergo further processing.

BRIEF DESCRIPTION OF THE DRAWING

The single FIGURE of the accompanying drawing, which is not limitative, is a flowsheet of the process for the pretreatment of light olefin fractions in accordance with the invention.

The fresh olefin charge stock ($C_3$–$C_4$ and/or $C_4$ fractions) to be treated is introduced through a line 1 into a tank 2, where it is dried on molecular sieves for the purpose of eliminating any traces of moisture which might react with the boron trifluoride to form borates.

After being mixed with gaseous boron trifluoride introduced through a line 5, the charge stock is conducted through a line 3 to a reactor 4. In view of the heat evolved in the reaction of the isobutene or of the butadiene with the boron trifluoride, the latter may advantageously be diluted with an inert gas such as nitrogen or argon, or even with butane or propane. With a view to increasing the contact surfaces and to retaining the heat generated by the reaction, the reactor 4 may contain an inert contact material, such as quartz pieces, glass beads, sand, alumina beads, pebbles, etc. Under the operating conditions set forth above, this contact material can be maintained at a temperature of about 20° C., for example.

The effluent from the reactor 4 is conducted through a line 6 to a flash drum 7, in which the boron trifluoride is separated overhead through a line 8 from the fraction being treated and optionally recycled to the reactor 4. At the bottom of the flash drum 7, the olefin fraction being treated, which contains polymers of butadiene and isobutene, is recovered through a line 9 and conducted to a separating column 10.

From the bottom of column 10, through a line 11, the isobutene and butadiene polymers are withdrawn, and from the top of the column, through a line 12, the $C_3$–$C_4$ or $C_4$ fractions which have been purified, i.e., freed of the unwanted isobutene and butadiene. The fractions so treated may be conducted through a line 12 to units for further processing, for example, dimerization, alkylation, oligomerization, etc., optionally after a treatment with soda for the removal of traces of residual boron trifluoride.

The process of the invention is applicable to any light $C_3$–$C_4$ and/or $C_4$ petroleum fraction, for example, to an olefinic fraction coming from a catalytic cracking unit.

The examples which follow will serve to illustrate the practice of the invention.

EXAMPLE 1

An olefinic charge stock coming from a catalytic cracking unit and having the composition given in the first column of Table 1 which follows was treated in accordance with the invention.

The treating conditions in reactor 4 were as follows:

| | |
|---|---|
| Temperature: | 20° C. |
| Pressure: | 30 bars |
| Hourly space velocity of charge stock: | 3 v/v/h |
| Feed rate of boron trifluoride (based on charge stock): | 2,000 ppm |
| Contact material: | 100 ml glass beads |

The gaseous effluent leaving the separating column 10 through line 12 had the composition given in the second column of Table 1 below.

TABLE 1

| | Charge (grams) | Effluent (grams) |
|---|---|---|
| Saturated $C_3$/$C_4$ hydrocarbons | 56.3 | 56.4 |
| Olefins including: | 43.7 | 32.2 |
| Butene-1 | 6.3 | 6.2 |
| Isobutene | 8.8 | 0.5 |
| Butenes-2 | 15.9 | 13.2 |
| Propylene | 12.6 | 12.3 |
| Butadiene | 0.06 | 0.02 |
| Polymers formed | 0 | 11.4 |
| Total | 100 | 100 |

Pretreatment in accordance with the present invention permitted the specific removal rates set forth in Table 2 below to be obtained for each olefin.

TABLE 2

| Specific olefin removal rate (Weight percent) | |
|---|---|
| Butene-1 | 1 |
| Isobutene | 94 |
| Butenes-2 | 17 |
| Propylene | 2 |
| Butadiene | 70 |

The polymers formed, which were withdrawn through line 11, had the following composition (in weight percent):

| | | |
|---|---|---|
| 100–120° C. fraction (diisobutene and homologs) | 10 | ⎫ |
| 120–220° C. fraction (triisobutene and homologs) | 27 | ⎬ 67 |
| 220–320° C. fraction (tetraisobutene and homologs) | 30 | ⎭ |
| Heavy polymers, 320° C. and up | 33 | |
| | 100 | |

EXAMPLE 2 a charge stock having the composition given in the first column of Table 3 which follows was treated in accordance with the invention.

This charge stock was subjected in reactor 4 to two series of tests under the following conditions:
Temperature: 20° C.
Pressure: 2 bars (Test A) and 4 bars (Test B)
Hourly space velocity of charge: 3 v/v/h Feed rate of boron trifluoride (based on charge stock): 2,000 ppm Contact material: 100 ml glass beads 2 mm in diameter The composition of the effluent (Tests A and B) leaving through line 12 is given in the second and third columns of Table 3 which follows:

TABLE 3

|  | Charge (grams) | Effluent (grams) | |
| --- | --- | --- | --- |
|  |  | Test A | Test B |
| Saturated C3/C4 hydrocarbons | 56.2 | 56.2 | 56.2 |
| Olefins including: | 43.8 | 32.7 | 33.0 |
| Butene-1 | 6.4 | 6.3 | 6.4 |
| Isobutene | 8.9 | 0.7 | 0.7 |
| Butenes-2 | 15.8 | 13.3 | 13.4 |
| Propylene | 12.7 | 12.4 | 12.5 |
| Butadiene | 0.05 | 0 | 0 |
| Polymers formed | 0 | 11.1 | 10.8 |
| Total | 100 | 100 | 100 |

Pretreatment in accordance with the invention permitted the specific removal rates set forth in Table 4 which follows to be obtained for each olefin.

TABLE 4

| | Specific olefin removal rate (Weight percent) | |
| --- | --- | --- |
|  | Test A | Test B |
| Butene-1 | 1.5 | 0.5 |
| Isobutene | 92 | 92 |
| Butenes-2 | 16 | 15 |
| Propylene | 2.5 | 2 |
| Butadiene | 100 | 100 |

The polymers formed, which were withdrawn through line 11, had the following composition (in weight percent):

| | Test A | Test B |
| --- | --- | --- |
| 100–120° C. fraction (diisobutene and homologs) | 13 | 12 |
| 120–220° C. fraction (triisobutene and homologs) | 26 } 65 | 28 } 66 |
| 220–320° C. fraction (tetraisobutene and homologs) | 26 | 26 |
| Heavy polymers, 320° C. and up | 35 | 34 |

The invention thus provides a process which is simple, and which is readily carried out since the operating conditions are not severe, for the removal of most of the isobutene and butadiene contained in a light petroleum fraction before the olefins contained in that fraction are subjected to an upgrading treatment such as oligomerization, dimerization, alkylation, etc.

We claim:

1. A process for the pretreatment of a light olefin fraction to selectively remove isobutene and butadiene, comprising:

contacting the olefin fraction with boron trifluoride in a gas phase at a temperature of from 0° to 100° C. and a pressure of from 0 to 50 bars to form polymers of isobutene and butadiene in an effluent; and separating the boron trifluoride and the polymers of isobutene and butadiene from the effluent.

2. A process according to claim 1, wherein the olefin fraction and the gaseous boron trifluoride are contacted in the presence of a filler material.

3. A process according to claim 2, wherein the olefin fraction and the gaseous boron trifluoride are contacted at a temperature between 0° and 100° C. and a pressure between 0 and 50 bars.

4. A process according to claim 1, wherein the boron trifluoride is separated from the effluent prior to separation of the polymers of isobutene and butadiene.

5. A process according to claim 2, wherein the boron trifluoride is separated from the effluent prior to separation of the polymers of isobutene and butadiene.

6. A process according to claim 4, wherein the boron trifluoride is separated from the effluent by flash-distillation.

7. A process according to claim 5, wherein the boron trifluoride is separated from the effluent by flash-distillation.

8. A process according to claim 1, wherein the polymers of isobutene and butadiene are separated from the effluent by fractionation.

9. A process according to claim 6, wherein the polymers of isobutene and butadiene are separated from the effluent by fractionation.

10. A process according to claim 7, wherein the polymers of isobutene and butadiene are separated from the effluent by fractionation.

11. A process according to 1, further comprising removing residual traces of boron trifluoride from the effluent after the separating step by treating the effluent with soda.

12. A process according to 9, further comprising removing residual traces of boron trifluoride from the effluent after the separating step by treating the effluent with soda.

13. A process according to 10, further comprising removing residual traces of boron trifluoride from the effluent after the separating step by treating the effluent with soda.

14. A process according to claim 1, further comprising recycling to the olefin fraction the boron trifluoride which has been separated from the effluent.

15. A process according to claim 2, further comprising recycling to the olefin fraction the boron trifluoride which has been separated from the effluent.

16. A process according to claim 3, further comprising recycling to the olefin fraction the boron trifluoride which has been separated from the effluent.

17. A process according to claim 12, further comprising recycling to the olefin fraction the boron trifluoride which has been separated from the effluent.

18. A process according to claim 13, further comprising recycling to the olefin fraction the boron trifluoride which has been separated from the effluent.

19. A process according to claim 1, wherein the concentration of boron trifluoride is 500 to 10,000 ppm of the olefin fraction.

20. A process according to claim 2, wherein the contacting step is carried out at an hourly space velocity of 0.1 to 10 volumes of olefin fraction per volume of filler material and per hour.

* * * * *